(12) United States Patent
Yang et al.

(10) Patent No.: US 8,071,674 B2
(45) Date of Patent: Dec. 6, 2011

(54) COMPOSITIONS HAVING HASE RHEOLOGY MODIFIERS

(75) Inventors: Hui Shirley Yang, Plainsboro, NJ (US);
Derek Pakenham, Hamilton, NJ (US);
Herve Adam, Clarksburg, NJ (US);
Pierre Hennaux, New York, NY (US)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 12/803,386

(22) Filed: Jun. 25, 2010

(65) Prior Publication Data
US 2010/0273683 A1 Oct. 28, 2010

Related U.S. Application Data

(63) Continuation of application No. 11/443,919, filed on May 31, 2006, now Pat. No. 7,772,421.

(60) Provisional application No. 60/686,083, filed on May 31, 2005.

(51) Int. Cl.
*C08L 31/02* (2006.01)
*C08L 33/10* (2006.01)

(52) U.S. Cl. ........ 524/502; 524/501; 524/556; 524/558; 525/55

(58) Field of Classification Search .................. 568/613; 560/205, 224; 525/191; 524/501, 502
See application file for complete search history.

(56) References Cited

U.S. PATENT DOCUMENTS

| | | | |
|---|---|---|---|
| 2,458,888 A | | 1/1949 | Rehberg et al. |
| 4,384,096 A | * | 5/1983 | Sonnabend .................. 526/313 |
| 4,620,028 A | * | 10/1986 | Gorman et al. ............... 560/193 |
| 4,668,410 A | | 5/1987 | Haas et al. |
| 4,830,769 A | * | 5/1989 | O'Lenick et al. ............. 508/497 |
| 5,294,693 A | | 3/1994 | Egraz et al. |
| 5,674,823 A | * | 10/1997 | Ricca et al. .................. 510/102 |
| 5,874,495 A | * | 2/1999 | Robinson et al. |
| 6,162,877 A | | 12/2000 | Sau |
| 6,846,798 B2 | | 1/2005 | Joye et al. |
| 2005/0002892 A1 | * | 1/2005 | Khan et al. |
| 2005/0175568 A1 | * | 8/2005 | Asari et al. |
| 2006/0135683 A1 | * | 6/2006 | Adam et al. |

FOREIGN PATENT DOCUMENTS

| | | | |
|---|---|---|---|
| EP | 226097 B1 | * | 9/1990 |
| EP | 705852 B1 | * | 12/1998 |
| EP | 1 949 888 A1 | * | 7/2008 |
| EP | 38 22 202 | * | 7/2009 |

OTHER PUBLICATIONS

Johansson (Speciality Chemicals Magazine, Nov 2004; online at http://www.firp.ula.ve/archivos/material_web_4xx/04_SCM_Johansson.pdf).*

C.E. Rehberg et al. "Preparation and Properties of Monomeric and Polymeric Acrylic Esters of Ether-Alcohols" Journal of Organic Chemistry, vol. 14, 1949, pp. 1094-1098, XP002594784.*

* cited by examiner

*Primary Examiner* — David W Wu
*Assistant Examiner* — Vu A Nguyen (57) ABSTRACT

A monomer compound that contains at least one polymerizable functional group per molecule, and at least one bicycloheptyl-, bicycloheptenyl-, or branched ($C_5$-$C_{42}$)alkyl-polyether radical per molecule, wherein the bicycloheptyl- or bicycloheptenyl-polyether radical may optionally be substituted on one or more of the ring carbon atoms by one or two ($C_1$-$C_6$)alkyl groups per ring carbon atom is useful in making polymers, particularly pH responsive polymers.

7 Claims, 3 Drawing Sheets

COMPOSITIONS HAVING HASE RHEOLOGY MODIFIERS

This application is a continuation of U.S. patent application Ser. No. 11/443,919, filed May 31, 2006, now U.S. Pat. No. 7,772,421, which claims the benefit of U.S. Provisional Patent Application Ser. No. 60/686,083, filed May 31, 2005.

BACKGROUND OF THE INVENTION

1. Field of Invention

The present invention relates to HASE rheological additives for aqueous systems and emulsions. More particularly, the present invention relates to a pH-responsive composition and a method useful for modifying the rheological properties of aqueous emulsions.

2. Description of Related Art

Rheological additives are chemical compositions, which, added even in small amounts, modify a liquid system's rheological properties, such as viscosity and response to shear. Such additives or thickeners may be used in a variety of liquid systems including aqueous systems such as paints, aqueous inks, and personal care products. The additives improve the rheological properties by also affecting the dispersion, suspension and emulsification of pigments, binders and other solids within a vehicle.

Conventional rheological additives include those of natural and synthetic origin. Useful natural thickeners include, for example, guar gum, pectin, xanthan gum, and alginate. Useful synthetic thickeners include, for example, hydrophobically modified ethoxylated urethanes (HEUR), ethylcellulose methylcellulose, hydroxyethylcellulose (HEC), hydroxymethylcellulose, carboxymethylcellulose, and other modified cellulosics.

Conventional natural and synthetic polymers have limitations with respect to use as thickeners in aqueous systems, particularly in paints and coatings. In general, they do not provide a rheological profile suitable for adequate viscosity control, splatter resistance and flow properties required in paints and coatings. For example, HEC swells rapidly in water and forms lumps, which are not readily dispersible.

Hydrophobically modified alkali soluble emulsion (HASE) polymer systems are commonly employed to modify the rheological properties of aqueous emulsion systems. Under the influence of a base, organic or inorganic, the HASE particles gradually swell and expand to form a three-dimensional network by intermolecular hydrophobic aggregation between HASE polymer chains and/or with components of the emulsion. This network, combined with the hydrodynamic exclusion volume created by the expanded HASE chains, produces the desired thickening effect. This network being sensitive to applied stress, breaks down under shear and recovers when the stress is relieved. Such rheological properties are particularly desirable for paints and coatings because they make the formulation easy to apply onto a surface while providing the thickness needed for uniform coverage and avoid spattering.

HASE polymer systems can be prepared from the following monomers: (a) an ethylenically unsaturated carboxylic acid, (b) a nonionic ethylenically unsaturated monomer, and (c) an ethylenically unsaturated hydrophobic monomer. Representative HASE polymer systems include those shown in EP 226097 B1, EP 705852 B1, U.S. Pat. No. 4,384,096, and U.S. Pat. No. 5,874,495.

Therefore, polymeric thickeners are desired in the industry as an alternative for HEC and similar cellulosics. Such paints should be non-biodegradable, free of toxic by-products, economical to manufacture, and exhibit excellent storage stability.

It would be desirable to have a HASE system wherein rheological properties are improved. In particular, it would be desirable to have a HASE system that provides enhanced rheological properties in paints and coatings. Further in particular, it would be desirable to have a HASE system that provides improved viscosity control, splatter resistance and flow properties in paints and coatings.

SUMMARY OF THE INVENTION

In a first aspect, the present invention is directed to a monomer compound comprising:

at least one polymerizable functional group per molecule, and at least one bicycloheptyl-, bicycloheptenyl-, or branched $(C_5-C_{42})$alkyl-polyether radical per molecule, wherein the bicycloheptyl- or bicycloheptenyl-polyether radical may optionally be substituted on one or more of the ring carbon atoms by one or two $(C_1-C_6)$alkyl groups per carbon atom.

In a second aspect, the present invention is directed to a polymer comprising one or more monomeric units, each comprising at least one bicycloheptyl-, bicycloheptenyl- or branched $(C_5-C_{42})$alkyl-polyether radical per molecule, wherein the bicycloheptyl- or bicycloheptenyl-polyether radical may optionally be substituted on one or more of the ring carbon atoms by one or two $(C_1-C_6)$alkyl groups per ring carbon atom.

In a third aspect, the present invention is directed to a pH responsive polymer, comprising, based on the total weight of monomers, (a) from about 25 to about 70 percent by weight acid monomeric units, each independently comprising a carboxylic acid-functional substituent group, (b) from about 30 to about 70 percent by weight nonionic monomeric units, each independently comprising a nonionic substituent group, and (c) from about 0.05 to about 20 percent by weight hydrophobic monomeric units, each independently comprising at least one bicycloheptyl-, bicycloheptenyl-, or branched $(C_5-C_{42})$alkyl-polyether radical per monomeric unit, wherein the bicycloheptyl- or bicycloheptenyl-polyether radical may optionally be substituted on one or more of the ring carbon atoms by one or two $(C_1-C_6)$alkyl groups per carbon atom.

In a fourth aspect, the present invention is directed to a pH-responsive composition having A) a solvent and B) a polymer dispersed therein. The polymer has the following:

(a) about 25 to about 70 weight percent based on total monomers of at least one $C_3$-$C_8$ alpha beta-ethylenically unsaturated carboxylic acid monomer of the structure (II):

$$RCH=C(R')COOH \qquad (II)$$

wherein R is H, $CH_3$, or —$CH_2COOX$; and wherein if R is H, then R' is H, $C_1$-$C_4$ alkyl, or —$CH_2COOX$; if R is —$C(O)OX$, then R' is H or —$CH_2C(O)OX$; or if R is $CH_3$, then R' is H; and X, if present, is H or $C_1$-$C_4$ alkyl;

(b) about 30 to about 70 weight percent based on total monomers of at least one copolymerizable non-ionic $C_2$-$C_{12}$ alpha beta-ethylenically unsaturated monomer of the structure (III):

$$H_2C=CYZ \qquad (III)$$

wherein Y is H, $CH_3$, or Cl; Z is CN, Cl, —COOR', —$C_6H_4R'$, —COOR", or —HC=$CH_2$; and wherein R is $C_1$-$C_8$ alkyl or $C_2$-$C_8$ hydroxy alkyl; and wherein R' is H, Cl, Br, or $C_1$-$C_4$ alkyl; and R" is $C_1$-$C_8$ alkyl; and (c) about 0.05 to about 20 weight percent based on total monomer weight of at least one ethylenically unsaturated monomer represented by the structure selected from a group consisting of structure IV and structure VI; wherein structure IV represents an ester of an alkoxylated fatty alcohol (IV)

wherein R is H or $CH_3$; wherein $R_1$ is a —$(CH_2)_pH$ alkyl chain; wherein p is an integer from 1 to about 4; wherein j is an Integer from 1 to about 50; wherein k is an integer from 0 to about 20; wherein h is 1 or 2; and wherein X has the following structure (V):

(V)

wherein m and n are, independently, are positive integers from 1 to 39 and m+n represents an integer from 4 to 40; and wherein structure VI; is an ester of an alkoxylated nopol (VI)

wherein $R_3$ is H or $CH_3$; $R_4$ is an alkyl chain containing 1 to about 4 carbons; M is an integer from 1 to about 50; and N is 0 or an integer of less than or equal to M.

The pH responsive polymer is useful for modifying the rheological properties of an aqueous composition, and can be added to an aqueous paint or coating composition to provide desirable properties, such as improved viscosity and flow control as well as improved spatter resistance.

The pH responsive polymer of the present invention is useful in, for example, personal care applications, such as shampoos, body wash, hand soap, lotions, creams, conditioners, shaving products, facial washes, neutralizing shampoos, personal wipes, and skin treatments, and in home care applications, such as liquid detergents, laundry detergents, hard surface cleansers, dish wash liquids, toilet bowl cleaners, as well as other applications, such as oil field and agrochemical applications.

In one embodiment, the present invention is directed to an aqueous composition, comprising water and the above described pH responsive polymer. In one embodiment, the aqueous composition exhibits viscoelastic properties.

It is a still yet further object of the invention to have compounds, i.e., monomers, corresponding to structures III and V. There may also be polymers and copolymers thereof that differ from the HASE polymers described above.

DETAILED DESCRIPTION OF THE INVENTION

As used herein, the terminology "($C_r$-$C_s$)" in reference to an organic group, wherein r and s are each integers, indicates that the group may contain from r carbon atoms to s carbon atoms per group.

As used herein, the term "alkyl" means a monovalent straight or branched saturated hydrocarbon radical, more typically, a monovalent straight or branched saturated ($C_1$-$C_{22}$)hydrocarbon radical, such as, for example, methyl, ethyl, n-propyl, isopropyl, n-butyl, isobutyl, tert-butyl, n-hexyl, n-octyl, and n-hexadecyl.

As used herein, the term "cycloalkyl" means a saturated ($C_5$-$C_{22}$)hydrocarbon radical that includes one or more cyclic alkyl rings, such as, for example, cyclopentyl, cycloheptyl, cyclooctyl, and "bicyloalkyl" means a cycloalkyl ring system that comprises two condensed rings, such as bicycloheptyl.

As used herein, the term "alkenyl" means an unsaturated straight or branched hydrocarbon radical, more typically an unsaturated straight, branched, ($C_2$-$C_{22}$) hydrocarbon radical, that contains one or more carbon-carbon double bonds, such as, for example, ethenyl, n-propenyl, iso-propenyl, As used herein, the term "cycloalkenyl" means an unsaturated ($C_5$-$C_{22}$) hydrocarbon radical, that contains one or more cyclic alkenyl rings, such as cyclohexenyl, cycloheptenyl, and "bicycloalkenyl" means a cycloalkenyl ring system that comprises two condensed rings, such as bicycloheptenyl.

The "bicyclo[d.e.f]" notation is used herein in reference to bicycloheptyl and bicycloheptenyl ring systems in accordance with the von Baeyer system for naming polycyclic compounds, wherein a bicyclic system is named by the prefix "bicyclo-" to indicate number of rings in the system, followed by a series of three arabic numbers, listed in descending numerical order, separated by full stops, and enclosed in square brackets, to indicate the respective number of skeletal atoms in each acyclic chain connecting the two common atoms (the "bridgehead atoms"), excluding the bridgehead atoms.

Suitable polymerizable functional groups include, for example, acrylo, methacrylo, acrylamido, methacrylamido, diallylamino, allyl ether, vinyl ether, α-alkenyl, maleimido, styrenyl, and α-alkyl styrenyl groups.

In one embodiment, the bicycloheptyl- or bicycloheptenyl- or branched $(C_5-C_{42})$alkyl-polyether radical is according structure (I):

(I)

wherein:
$R^{11}$ is bicycloheptyl, bicycloheptenyl, or branched $(C_5-C_{42})$alkyl, wherein the bicycloheptyl or bicycloheptenyl group may optionally be substituted on one or more of the ring carbon atoms by one or two $(C_1-C_6)$alkyl groups per ring carbon atom,
$R^{12}$ is absent, or is a bivalent linking group, and
$R^{13}$ is a bivalent polyether group.

In one embodiment, $R^{11}$ is a branched alkyl group according to structure (VII):

(VII)

wherein:
$R^{19}$ and $R^{20}$ are each independently $(C_1-C_{40})$alkyl, and b is an integer of from 0 to 39, provided that $R^{11}$, that is, $R^{19}$, $R^{20}$ and the $—(CH_2)_b—$ radical taken together, comprises a total of from about 6 to about 42, more typically about 12 to about 42, carbon atoms.

In one embodiment, $R^{11}$ is bicyclo[d.e.f]heptyl or bicyclo[d.e.f]heptenyl, wherein d is 2, 3, or 4, e is 1 or 2, f is 0 or 1, and the sum of d+e+f=5, and which may, optionally, be substituted on one or more of the ring carbon atoms by one or more $(C_1-C_6)$alkyl groups. More typically, $R^{11}$ is:
(i) a bicyclo[3.1.1]heptyl or bicyclo[3.1.1]heptenyl group that is bonded to $R^{12}$, if present, or to $R^{13}$, if $R^{12}$ is not present, via its carbon atom at the 2-position and is typically substituted on its carbon atom at the 6-position by one or two $(C_1-C_6)$alkyl radicals, more typically by two methyl radicals, or
(ii) a bicyclo[3.1.1]heptyl or bicyclo[2.2.1]heptenyl group that is bonded to $R^{12}$, if present, or to $R^{13}$, if $R^{12}$ is not present, via its carbon atom at the 2-position or 3-position and is typically substituted on its carbon atom at the 7 position by one or two $(C_1-C_6)$alkyl radicals, more typically by two methyl radicals, In one embodiment, $R^{12}$ is a bivalent oxyalkylene or oxyalkylene oxy radical which may optionally be substituted on one or more carbon atoms of the radical with alkenyl, cycloalkyl, or cycloalkenyl. In one embodiment, $R^{12}$ is $—OC_vH_{2v}—$, wherein v is an integer of from 1 to 10, more typically from 1 to 6, even more typically from 2 to 4. In one embodiment, $R^{12}$ is or $—O—CH(R^{16})—CH(R^{17})—O—$, wherein $R^{14}$, $R^{15}$, $R^{16}$, and $R^{17}$ are each independently H, alkyl, alkenyl, cycloalkyl or cycloalkenyl, more typically H, $(C_1-C_6)$alkyl, or $(C_1-C_6)$alkenyl, and even more typically H, methyl, or ethyl.

In one embodiment, $R^{13}$ is a bivalent polyoxyalkylene group according to structure (VIII):

(VIII)

wherein:
p' and q are independently integers of from 2 to 5, more typically 2 or 3,
each r is independently an integer of from 0 to about 80, more typically from 0 to about 50,
each s is independently an integer of from 1 to about 80, more typically from about 1 to about 50, and
t is an integer of from 1 to 50, provided that the product of t multiplied times the sum of r+s is less than or equal to about 100.

In embodiments wherein $—(OC_{p'}H_{2p'})—$ and $(—OC_qH_{2q})—$, oxyalkylene units with p' not equal to q, are each present, the respective oxylakylene units may be arranged randomly, in blocks, or in alternating order.

In one embodiment, the monomer of the present invention is according to structure (IX):

$R^{18}—R^{13}—R^{12}—R^{11}$ (IX)

wherein:
$R^{11}$, $R^{12}$, and $R^{13}$ are each defined as above, and
$R^{18}$ is acrylo, methacrylo, acrylamido, methacrylamido, diallylamino, allyl ether, vinyl ether, α-alkenyl, maleimido, styrenyl, or α-alkyl styrenyl.

In one embodiment, $R^{18}$ is acrylo or methacrylo.

In one embodiment, the monomer of the present invention is a compound according to structure (X):

(X)

wherein $R^{21}$ is H or methyl, and $R^{19}$, $R^{20}$, b, p', q, r, s, and t are each as described above.

In one embodiment, the monomer of the present invention is a compound according to structure (XI):

(XI)

wherein $R^{21}$ is H or methyl, and p', q, r, s, and t are each as described above.

Suitable bicycloheptyl- and bicycloheptenyl-moieties may be derived from, for example, terpenic compounds having core (non-substituted) 7 carbon atom bicyclic ring systems according to structures (XII)-(XVII):

[3.2.0]

(XII)

[2.2.1]

(XIII)

[4.1.0]

(XIV)

[3.1.1]

(XV)

[3.1.1]

(XVI)

[4.1.0]

(XVII)

For example, a bicycloheptenyl intermediate compound (XVIII), known as "Nopol":

(XVIII)

is made by reacting β-pinene with formaldehyde, and
a bicycloheptyl intermediate compound (XIX), known as "Arbanol:

(XIX)

is made by isomerization of α-pinene to camphene and ethoxyhydroxylation of the camphene.

In one embodiment, a bicycloheptyl- or bicycloheptenyl-intermediate is alkoxylated by reacting the bicycloheptyl- or bicycloheptenyl intermediate with one or more alkylene oxide compounds, such as ethylene oxide or propylene oxide, to form a bicycloheptyl-, or bicycloheptenyl-polyether intermediate. The alkoxylation may be conducted according to well known methods, typically at a temperature in the range of about 100° to about 250° C. and at a pressure in the range of from about 1 to about 4 bars, in the presence of a catalyst, such as a strong base, an aliphatic amine, or a Lewis acid, and an inert gas, such as nitrogen or argon.

The bicycloheptyl-, or bicycloheptenyl-polyether monomer is then formed by addition of a polymerizable functional group to the bicycloheptyl- or bicycloheptenyl-polyether intermediate, by, for example, esterification, under suitable reaction conditions, of the bicycloheptyl- or bicycloheptenyl-polyether intermediate with, for example, methacrylic anhydride.

Alternatively, a monomer comprising a polymerizable functional group, such as for example, polyethylene glycol monomethacrylate, can be alkoxylated to form a polyether monomer and the alkoxylated monomer then reacted with the bicycloheptyl- or bicycloheptenyl-intermediate to form the bicycloheptyl-, or bicycloheptenyl-polyether monomer.

In one embodiment, the polymer of the present invention comprises from about 30 to about 65, more typically from about 30 to about 60, percent by weight acid monomeric units, from about 35 to about 70, more typically from about 40 to about 60, percent by weight nonionic monomeric units, and from about 1 to about 15, more typically from about 2 to about 10, percent by weight hydrophobic monomeric units.

The present invention provides a pH-responsive composition useful for modifying the rheological properties of an aqueous emulsion.

In one embodiment, the acid monomer units of the pH responsive polymer are derived from one or more ethylenically unsaturated carboxylic acid monomer, such as, for example, methacrylic acid.

In one embodiment, the nonionic monomer units of the pH responsive polymer are derived from one or more ethylenically unsaturated nonionic monomer, such as an alkyl or hydroxyalkyl ester of an acid monomer, for example, 2-ethylhexylacrylate.

In one embodiment, the hydrophobic monomeric units of the polymer of the present invention each comprise a pendant substituent group according to structure (I), wherein $R^{11}$, $R^{12}$, and $R^{13}$ are each as described above.

In one embodiment, the polymer of the present invention is prepared from the following components: (A) about 25 to 70 weight percent based on total monomers of a $C_3$-$C_8$ alpha beta-ethylenically unsaturated carboxylic acid monomer; (B) about 30 to 70 weight percent based on total monomers of at least one copolymerizable non-ionic $C_2$-$C_{12}$ alpha beta-ethylenically unsaturated monomer, and (C) about 0.05 to about 20 weight percent based on total monomer weight of a selected hydrophobic ethylenically unsaturated monomer.

The effectiveness of these liquid emulsion polymers as a pH-responsive thickener for many aqueous products is dependent on the characteristics of each monomer. Component A provides the requisite pH-responsiveness and hydrophilicity. Component B provides an extended polymer backbone and allows adjustment of the hydrophilic/lipophilic balance. Component C provides an in situ, bound surfactant to control the rheology of the aqueous system containing the solubilized polymeric thickener. The proportions of the individual monomers can be varied to achieve optimum properties for specific applications.

Component A is at least one $C_3$-$C_8$ alpha beta-ethylenically unsaturated carboxylic acid monomer of the structure (II):

$$RCH=C(R')COOH \qquad (II)$$

wherein if R is H, then R' is H, $C_1$-$C_4$ alkyl, or —$CH_2COOX$; if R is —C(O)OX, then R' is H or —$CH_2C(O)OX$; or if R is $CH_3$, then R' is H; and X, if present, is H or $C_1$-$C_4$ alkyl.

Carboxylic acids useful as an ethylenically unsaturated carboxylic acid monomer and as component (A) include itaconic acid, fumaric acid, crotonic acid, acrylic acid, methacrylic acid, and maleic acid. A preferred carboxylic acid monomer is methacrylic acid or a mixture thereof with one or more other carboxylic acids. Half esters are also suitable.

Component A is present at about 25 to 70, preferably about 30 to about 65, and most preferably about 35 to about 60 weight percent based on total monomer weight of components A, B, and C.

Component B is at least one copolymerizable non-ionic $C_2$-$C_{12}$ alpha beta-ethylenically unsaturated monomer of the structure (III):

$$H_2C=CYZ \qquad (III)$$

wherein Y is H, $CH_3$, or Cl; Z is CN, Cl, —COOR', —$C_6H_4R'$, —COOR, or —HC=$CH_2$; R is $C_1$-$C_8$ alkyl or $C_2$-$C_8$ hydroxy alkyl; R' is H, Cl, Br, or $C_1$-$C_4$ alkyl, and R" is $C_1$-$C_8$ alkyl.

Monomers useful as the ethylenically unsaturated nonionic monomer and as component B include, but are not limited to, $C_1$-$C_8$ alkyl and $C_2$-$C_8$ hydroxyalkyl esters of acrylic and methacrylic acid. Useful monomers include ethyl acrylate, ethyl methacrylate, methyl methacrylate, 2-ethylhexyl acrylate, butyl acrylate, butyl methacrylate, 2-hydroxyethyl acrylate, 2-hydroxybutyl methacrylate, styrene, vinyltoluene, t-butylstyrene, isopropylstyrene, and p-chlorostyrene, vinyl acetate, vinyl butyrate, vinyl caprolate; acrylonitrile, methacrylonitrile, butadiene, isoprene, vinyl chloride, vinylidene chloride, and combinations thereof. A preferred monomer is ethyl acrylate alone or in combination with styrene, hydroxyethyl acrylate, acrylonitrile, vinyl chloride or vinyl acetate.

Component B is present at about 30 to about 70, preferably about 35 to about 70, and more preferably from about 40 to about 60 weight percent based on total monomer weight of components A, B, and C. Preferably, the hydrophilic balance of the copolymer product can be adjusted by the appropriate selection of the unsaturated nonionic monomer.

Component C is at least one hydrophobic ethylenically unsaturated monomer selected from among those represented in structure (IV) or structure (VI). Structure (IV) has the following structure:

wherein R is H or $CH_3$; wherein $R_1$ is a —$(CH_2)_p$H alkyl chain; wherein p is an integer from 1 to about 4; wherein j is an integer from 1 to about 50 and preferably about 10 to about 40; wherein k is an integer from 0 to about 20, wherein h is 1 or 2 and wherein X has the following structure (V):

wherein m and n are independently positive integers, and m+n represent an integer from 4 to 40 and preferably 4 to 20. In a preferred structure, k is equal to 0, l equal to is 25, h is equal to 1, n is equal to 8, and m is equal to 10.

Branched esters corresponding to component B are preferably synthesized from Guerbet alcohols. These alcohols have a branched structure and exhibit oxidative stability at elevated temperatures.

Structure (VI) has the following structure:

wherein $R_3$ is H or $CH_3$; $R_4$ is an alkyl chain containing 1 to about 4 carbons; M is an integer from 1 to about 50 and preferably about 10 to about 40; and N is an integer having a value of 0 or an integer less than or equal to M. In a most preferred structure, $R_3$ and $R_4$ are $CH_3$, M is equal to 25 and N is equal to 5.

Component C is present at about 0.05 to about 20, preferably about 1 to about 15, and most preferably about 2 to about 10 weight percent based on total monomer weight of components A, B, and C.

In one embodiment, the polymer composition of the present invention has a solids content of up to about 60 wt % and, more typically about 20 to about 50 wt %, based on the combined weight of the polymer of the present invention (including components A, B, and C) and emulsifiers/surfactants employed.

In one embodiment, the polymer composition of the present invention is in the form of an aqueous colloidal polymer dispersion. When the polymer composition is in the form of an aqueous colloidal polymer dispersion, the composition is maintained at a pH of about 5 or less to maintain stability. More typically, the aqueous colloidal polymer dispersion composition has a pH of about 2 to about 3. When thickening of the composition is desired, the pH of the composition can be increased to a value above about 5 by addition of a base to solubilize the polymer.

The polymer and polymer composition of the present invention can be conveniently prepared from the above-described monomers by conventional emulsion polymerization techniques at an acid pH of about 5.0 or less using free-radical producing initiators, usually in an amount from 0.01 percent to 3 percent based on the weight of the monomers. Polymerization at an acid pH of about 5.0 or less permits direct preparation of an aqueous colloidal dispersion having relatively high solids content without the problem of excessive viscosity.

The free-radical producing initiators typically are peroxygen compounds. Useful peroxygen compounds include inorganic persulfate compounds such as ammonium persulfate, potassium persulfate, sodium persulfate; peroxides such as hydrogen peroxide; organic hydroperoxides, for example, cumene hydroperoxide, and t-butyl hydroperoxide; organic peroxides, for example, benzoyl peroxide, acetyl peroxide, lauroyl peroxide, peracetic acid, and perbenzoic acid (sometimes activated by a water-soluble reducing agent such as ferrous compound or sodium bisulfite); and other free-radical producing materials or techniques such as 2,2'-azobisisobutyronitrile and high energy radiation sources.

Optionally, a chain transfer agent can be used. Representative chain transfer agents are carbon tetrachloride, bromoform; bromotrichloromethane; and long-chain alkyl mercaptans and thioesters, such as n-dodecyl mercaptan, t-dodecyl mercaptan, octyl mercaptan, tetradecyl mercaptan, hexadecyl mercaptan, butyl thioglycolate, isooctyl thioglycolate, and dodecyl thioglycolate. The chain transfer agents can be used in amounts up to about 10 parts per 100 parts of polymerizable monomers.

The composition has one or more emulsifiers. Useful emulsifiers include anionic surfactants, nonionic surfactants, amphoteric surfactants, and zwitterionic surfactants. Preferred surfactants are anionic surfactants. Examples of anionic emulsifiers are the alkali metal alkyl aryl sulfonates, the alkali metal alkyl sulfates and the sulfonated alkyl esters. Specific examples of these well-known emulsifiers are sodium dodecylbenzenesulfonate, sodium disecondary-butylnaphthalene sulfonate, sodium lauryl sulfate, disodium dodecyldiphenyl ether disulfonate, disodium n-octadecylsulfosuccinamate and sodium dioctylsulfosuccinate. Useful nonionic emulsifiers include, for example, common structures based on polyethylene oxide or oligosaccharides hydrophilic heads.

Optionally, other ingredients well known in the emulsion polymerization art may be included, such as chelating agents, buffering agents, inorganic salts and pH adjusting agents.

Usually the copolymerization is carried out at a temperature between about 60° C. and 90° C., but higher or lower temperatures may be used. The polymerization can be carried out batchwise, stepwise or continuously with batch and/or continuous addition of the monomers in a conventional manner.

The monomers can be copolymerized in such proportions, and the resulting emulsion polymers can be physically blended, to give products with the desired balance of properties for specific applications. For example, if a more viscous product is desired, the acid and surfactant monomer content can be increased. Greater flexibility and coalescence can be obtained with higher amounts of ethyl acrylate. Addition of styrene as a second nonionic vinyl monomer will increase to a higher pH the adjustment required to dissolve the emulsion in an aqueous coating composition. Minor quantities of a polyfunctional monomer, such as itaconic or fumaric acid or isoprene to introduce a higher carboxylic acid content or limited crosslinking, provide further control of the solubility of the emulsion polymer after pH adjustment.

Thus, by varying the monomers and their proportions, emulsion polymers having optimum properties for particular applications can be designed. Particularly effective liquid emulsion polymer thickeners are obtained by copolymerization of about 40 to about 50 weight percent of methacrylic acid, about 35 to about 50 weight percent of ethyl acrylate, and about 0.05 to 20 weight percent of the ester according to structures III and IV.

The copolymer products according to the present invention prepared by emulsion polymerization at an acid pH are in the form of stable aqueous colloidal dispersions containing the copolymer dispersed as discrete particles having average particle diameters of about 500 to about 3000 Å and preferably about 1000 to about 1750 Å as measured by light scattering. Dispersions containing polymer particles smaller than about 500 Å are difficult to stabilize, while particles larger than about 3000 Å reduce the ease of dispersion in the aqueous products to be thickened.

These emulsion copolymers according to the present invention will normally have number average molecular weights of at least about 30,000 daltons as determined by gel permeation chromatography. In one embodiment, the pH responsive polymer of the present invention exhibited a number average molecular weight of from about 30,000 to about 5,000,000 daltons, more typically from about 100,000 to about 2,000,000 daltons, even more typically from about 1,000,000 to about 1,000,000 daltons. To provide most effective thickening with copolymers that are water-soluble when neutralized, molecular weights within the range of about 200,000 to about 5,000,000 daltons are preferred. In terms of a standard Brookfield viscosity measured as a 1 percent aqueous solution in ammonium salt form at pH 9 and 25° C., a polymer with a viscosity of about 100 to about 1,000,000 cps, and preferably about 100 to about 300,000 cps, is particularly desirable for many applications. The aqueous dispersions of the copolymers contain about 10-50 weight percent of polymer solids and are of relatively low viscosity. They can be readily metered and blended with aqueous product systems.

The polymers and polymer compositions according to the present invention are pH-responsive. At the lower pH levels at which the emulsion polymerization takes place, i.e., pH levels of 5 or less, the composition is relatively thin or non-viscous. When the pH of the polymer dispersion is neutralized or adjusted by addition of a base to a pH of about 5.5 or more, preferably about 6.5 to about 11, the composition thickens substantially. The composition turns from semi-opaque or opaque to translucent or transparent as viscosity increases. Viscosity increases as polymer dissolves partially or completely in the aqueous phase of the composition. Neutralization can occur in situ when the emulsion polymer is blended with the base and added to the aqueous phase. Or, if desired for a given application, neutralization can be carried out when blending with an aqueous product. Useful bases include, but are not limited to, ammonia, an amine, sodium hydroxide, potassium carbonate or the like.

In addition to emulsion polymerization, polymers according to the present invention can also be made using known solution polymerization techniques. The monomers can be dissolved in an appropriate solvent such as toluene, xylene, tetrahydrofuran, or mixtures thereof. Polymerization can be accomplished in the time and at the temperature necessary, e.g., 60° C. to 80° C. and about 2 to 24 hours. The product can be obtained through normal techniques, including solvent stripping.

The polymers and polymer compositions according to the present invention are useful as water-soluble thickeners for a wide variety of applications ranging from cosmetics to oilfield drilling fluids, but are particularly useful for aqueous paints and coatings. Solution-polymerized polymers can be used in solvent systems or emulsified by known techniques for use in aqueous systems. Other uses include latexes and detergents. Useful cosmetic compositions will typically have an aqueous carrier, a pigment and/or cosmetic active, a HASE emulsion polymer, and optional adjuvants. Useful detergents and cleansers will typically have aqueous carrier, a HASE emulsion polymer, and optional adjuvants. Oilfield drilling fluids will typically have an aqueous carrier, HASE emulsion polymer as a thickener/viscosity modifier, and optional adjuvants. The oilfield drilling fluids are injected into the oilfield formation. Useful latex coatings will typically have an aqueous carrier, a HASE emulsion polymer, and optional adjuvants.

The HASE emulsion polymers according to the present invention as described herein are particularly useful as thickeners for a wide variety of water-based compositions. Such compositions include brine, slurries, and colloidal dispersions of water-insoluble inorganic and organic materials, such as natural rubber, synthetic or artificial latexes. The emulsion polymers of the invention are especially useful in areas requiring thickening at neutral pHs, such as in cosmetics.

In one embodiment, the aqueous composition comprising the pH responsive polymer of the present invention exhibits viscoelastic properties at neutral to alkaline pH values, typically at pH values greater than or equal to about 5, more typically greater than or equal to about 5.5, even more typically of from about 6 to about 9.

Synthetic latexes take the form of aqueous dispersions/suspensions of particles of latex polymers. Synthetic latexes include aqueous colloidal dispersions of water-insoluble polymers prepared by emulsion polymerization of one or more ethylenically unsaturated monomers. Typical of such synthetic latexes are emulsion copolymers of monoethylenically unsaturated compounds, such as styrene, methyl methacrylate, acrylonitrile with a conjugated diolefin, such as butadiene or isoprene; copolymers of styrene, acrylic and methacrylic esters, copolymers of vinyl halide, vinylidene halide, vinyl acetate and the like. Many other ethylenically unsaturated monomers or combinations thereof can be emulsion polymerized to form synthetic latexes. Such latexes are commonly employed in paints (latex paints) and coatings. The composition of the present invention may be added to latexes to modify/increase viscosity.

The polymeric thickeners of this invention are advantageous for use with the water-based compositions according to the foregoing description and with compositions containing those materials, especially coating compositions of various types. Mixtures or combinations of two or more thickeners may be used, if desired. Of course the latex polymers used in coating compositions are preferably film-forming at temperatures about 25° C. or less, either inherently or through the use of plasticizers. Such coating compositions include water-based consumer and industrial paints; sizing, adhesives and other coatings for paper, paperboard, textiles; and the like.

Latex paints and coatings may contain various adjuvants, such as pigments, fillers and extenders. Useful pigments include, but are not limited to, titanium dioxide, mica, and iron oxides. Useful fillers and extenders include, but are not limited to, barium sulfate, calcium carbonate, clays, talc, and silica. The compositions of the present invention described herein are compatible with most latex paint systems and provide highly effective and efficient thickening.

The polymer compositions of the present invention may be added to aqueous product systems at a wide range of amounts depending on the desired system properties and end use applications. In latex paints, the composition is added such that the emulsion (HASE) polymer according to the present invention is present at about 0.05 to about 5.0 weight percent and preferably about 0.1 to about 3.0 weight percent based on total weight of the latex paint, including all of its components, such as water, HASE polymer, latex polymer, pigment, and any adjuvants.

In formulating latexes and latex paints/coatings, physical properties that may be considered include, but are not limited to, viscosity versus shear rate, ease of application to surface, spreadability, and shear thinning.

The pH responsive polymer of the present invention is suitable in the preparation of personal care (cosmetics, toiletries, health and beauty aids, cosmeceuticals) and topical health care products, including without limitation, hair care products, such as shampoos (including combination shampoos, such as "two-in-one" conditioning shampoos); post-shampoo rinses; setting and style maintenance agents including setting aids, such as gels and sprays, grooming aids, such as pomades, conditioners, perms, relaxers, hair smoothing products, and the like; skin care products (facial, body, hands, scalp and feet), such as creams, lotions, conditioners, and cleansing products; anti-acne products; anti-aging products (exfoliant, keratolytic, anticellulite, antiwrinkle, and the like); skin protectants such as sunscreens, sunblock, barrier creams, oils, silicones, and the like; skin color products (whiteners, lighteners, sunless tanning accelerators, and the like); hair colorants (hair dyes, hair color rinses, highlighters, bleaches and the like); pigmented skin colorants (face and body makeups, foundation creams, mascara, rouge, lip products, and the like); bath and shower products (body cleansers, body wash, shower gel, liquid soap, soap bars, syndet bars, conditioning liquid bath oil, bubble bath, bath powders, and the like); nail care products (polishes, polish removers, strengtheners, lengtheners, hardeners, cuticle removers, softeners, and the like); and any aqueous acidic to basic composition to which an effective amount of the associative polymer can be incorporated for achieving a beneficial or desirable, physical or chemical, effect therein during storage and/or usage.

In one embodiment, the present invention is directed to a personal care composition comprising water, one or more surfactants, and a pH responsive polymer according to the present invention.

In one embodiment, the personal care composition comprises, based on 100 parts by weight ("pbw") of the personal care composition, from about 10 to about 80 pbw, more typically from about 20 to about 70 pbw, water, from about 1 to about 50 pbw of one or more surfactants and from about 0.05 to about 20 pbw of the pH responsive polymer of the present invention.

Suitable surfactants include anionic surfactants, cationic surfactants, non-ionic surfactants, zwitterionic surfactants, and mixtures thereof.

Suitable anionic surfactants are known compounds and include, for example, linear alkylbenzene sulfonates, alpha olefin sulfonates, paraffin sulfonates, alkyl ester sulfonates, alkyl sulfates, alkyl alkoxy sulfates, alkyl sulfonates, alkyl alkoxy carboxylates, alkyl alkoxylated sulfates, monoalkyl phosphates, dialkyl phosphates, sarcosinates, isethionates, and taurates, as well as mixtures thereof, such as for example, ammonium lauryl sulfate, ammonium laureth sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium trideceth sulfate, sodium tridecyl sulfate, ammonium trideceth sulfate, ammonium tridecyl sulfate, sodium cocoyl isethionate, disodium laureth sulfosuccinate, sodium methyl oleoyl taurate, sodium laureth carboxylate, sodium trideceth carboxylate, sodium monoalkyl phosphate, sodium dialkyl phosphate, sodium lauryl sarcosinate, lauroyl sarcosine, cocoyl sarcosinate, ammonium cocyl sulfate, sodium cocyl sulfate, potassium cocyl sulfate, monoethanolamine cocyl sulfate, sodium tridecyl benzene sulfonate, sodium dodecyl benzene sulfonate, and mixtures thereof.

The cationic counterion of the anionic surfactant is typically a sodium cation but may alternatively be a potassium, lithium, calcium, magnesium, ammonium cation, or an alkyl ammonium anion having up to 6 aliphatic carbon atoms, such as anisopropylammonium, monoethanolammonium, diethanolammonium, or triethanolammonium cation. Ammonium and ethanolammonium salts are generally more soluble than the sodium salts. Mixtures of the above cations may be used.

Suitable cationic surfactants are known compounds and include, for example, mono-cationic surfactants according to structure (XX) below:

(XX)

wherein:
$R^{31}$, $R^{32}$, $R^{33}$ and $R^{34}$, are independently hydrogen or an organic group, provided that at least one of $R^{31}$, $R^{32}$, $R^{33}$ and $R^{34}$ is not hydrogen, and
$X^-$ is an anion,
as well as mixtures of such compounds If one to three of the $R^{31}$, $R^{32}$, $R^{33}$ and $R^{34}$ groups are each hydrogen, then the compound may be referred to as an amine salt. Some examples of cationic amine salts include polyethoxylated (2) oleyl/stearyl amine, ethoxylated tallow amine, cocoalkylamine, oleylamine, and tallow alkyl amine.

For quaternary ammonium compounds (generally referred to as quats) $R^{31}$, $R^{32}$, $R^{33}$ and $R^{34}$ may be the same or different organic group, but may not be hydrogen. In one embodiment, $R^{31}$, $R^{32}$, $R^{33}$ and $R^{34}$ are each $C_8$-$C_{24}$ branched or linear hydrocarbon groups which may comprise additional functionality such as, for example, fatty acids or derivatives thereof, including esters of fatty acids and fatty acids with alkoxylated groups; alkyl amido groups; aromatic rings; heterocyclic rings; phosphate groups; epoxy groups; and hydroxyl groups. The nitrogen atom may also be part of a heterocyclic or aromatic ring system, e.g., cetethyl morpholinium ethosulfate or steapyrium chloride.

Examples of quaternary ammonium compounds of the monoalkyl amine derivative type include: cetyl trimethyl ammonium bromide (also known as CETAB or cetrimonium bromide), cetyl trimethyl ammonium chloride (also known as cetrimonium chloride), myristyl trimethyl ammonium bromide (also known as myrtrimonium bromide or Quaternium-13), stearyl dimethyl benzyl ammonium chloride (also known as stearalkonium chloride), oleyl dimethyl benzyl ammonium chloride, (also known as olealkonium chloride), lauryl/myristryl trimethyl ammonium methosulfate (also known as cocotrimonium methosulfate), cetyl dimethyl (2)hydroxyethyl ammonium dihydrogen phosphate (also known as hydroxyethyl cetyldimonium phosphate), babassuamidopropalkonium chloride, cocotrimonium chloride, distearyldimonium chloride, wheat germ-amidopropalkonium chloride, stearyl octyldimonium methosulfate, isostearaminopropalkonium chloride, dihydroxypropyl PEG-5 linoleaminium chloride, PEG-2 stearmonium chloride, Quaternium 18, Quaternium 80, Quaternium 82, Quaternium 84, behentrimonium chloride, dicetyl dimonium chloride, behentrimonium methosulfate, tallow trimonium chloride and behenamidopropyl ethyl dimonium ethosulfate.

Quaternary ammonium compounds of the dialkyl amine derivative type include, for example, distearyldimonium chloride, dicetyl dimonium chloride, stearyl octyldimonium methosulfate, dihydrogenated palmoylethyl hydroxyethylmonium methosulfate, dipalmitoylethyl hydroxyethylmonium methosulfate, dioleoylethyl hydroxyethylmonium methosulfate, hydroxypropyl bisstearyldimonium chloride, and mixtures thereof.

Quaternary ammonium compounds of the imidazoline derivative type include, for example, isostearyl benzylimidonium chloride, cocoyl benzyl hydroxyethyl imidazolinium chloride, cocoyl hydroxyethylimidazolinium PG-chloride phosphate, Quaternium 32, and stearyl hydroxyethylimidonium chloride, and mixtures thereof.

Typical cationic surfactants comprise dialkyl derivatives such as dicetyl dimonium chloride and distearyldimonium chloride; branched and/or unsaturated cationic surfactants such as isostearylaminopropalkonium chloride or olealkonium chloride; long chain cationic surfactants such as stearalkonium chloride and behentrimonium chloride; as well as mixtures thereof.

Suitable anionic counterions for the cationic surfactant include, for example, chloride, bromide, methosulfate, ethosulfate, lactate, saccharinate, acetate and phosphate anions.

Suitable nonionic surfactants are known compounds and include amine oxides, fatty alcohols, alkoxylated alcohols, fatty acids, fatty acid esters, and alkanolamides. Suitable amine oxides comprise, ($C_{10}$-$C_{24}$) saturated or unsaturated branched or straight chain alkyl dimethyl oxides or alkyl amidopropyl amine oxides, such as for example, lauramine oxide, cocamine oxide, stearamine oxide, stearamidopropylamine oxide, palmitamidopropylamine oxide, decylamine oxide as well as mixtures thereof. Suitable fatty alcohols include, for example, ($C_{10}$-$C_{24}$) saturated or unsaturated branched or straight chain alcohols, more typically ($C_{10}$-$C_{20}$) saturated or unsaturated branched or straight chain alcohols, such as for example, decyl alcohol, lauryl alcohol, myristyl alcohol, cetyl alcohol, stearyl alcohol, oleyl alcohol, linoleyl alcohol and linolenyl alcohol, and mixtures thereof. Suitable alkoxylated alcohols include alkoxylated, typically ethoxylated, derivatives of ($C_{10}$-$C_{24}$) saturated or unsaturated branched or straight chain alcohols, more typically ($C_{10}$-$C_{20}$) saturated or unsaturated branched or straight chain alcohols, which may include, on average, from 1 to 22 alkoxyl units per molecule of alkoxylated alcohol, such as, for example, ethoxylated lauryl alcohol having an average of 5 ethylene oxide units per molecule. Mixtures of these alkoxylated alcohols may be used. Suitable fatty acids include ($C_{10}$-$C_{24}$) saturated or unsaturated carboxylic acids, more typically ($C_{10}$-$C_{22}$) saturated or unsaturated carboxylic acids, such as, for example, lauric acid, oleic acid, stearic acid, myristic acid, cetearic acid, isostearic acid, linoleic acid, linolenic acid, ricinoleic acid, elaidic acid, arichidonic acid, myristoleic acid, and palmitoleic acid, as well as neutralized versions thereof. Suitable fatty acid esters include esters of ($C_{10}$-$C_{24}$) saturated or unsaturated carboxylic acids, more typically ($C_{10}$-$C_{22}$) saturated or unsaturated carboxylic acids, for example, propylene glycol isostearate, propylene glycol oleate, glyceryl isostearate, and glyceryl oleate, and mixtures thereof. Suitable alkanolamides include aliphatic acid alkanolamides, such as cocamide MEA (coco monoethanolamide) and cocamide MIPA (coco monoisopropanolamide), as well as alkoxylated alkanolamides, and mixtures thereof.

Suitable amphoteric surfactants are known compounds and include for example, derivatives of aliphatic secondary and tertiary amines in which the aliphatic radical can be straight chain or branched and wherein one of the aliphatic substituents contains from about 8 to about 18 carbon atoms and one contains an anionic water-solubilizing group as well as mixtures thereof. Specific examples of suitable amphoteric surfactants include the alkali metal, alkaline earth metal, ammonium or substituted ammonium salts of alkyl amphocarboxy glycinates and alkyl amphocarboxypropionates, alkyl amphodipropionates, alkyl amphodiacetates, alkyl amphoglycinates, and alkyl amphopropionates, as well as alkyl iminopropionates, alkyl iminodipropionates, and alkyl amphopropylsulfonates, such as for example, cocoamphoacetate cocoamphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, and stearoamphoacetate.

In one embodiment, the amphoteric surfactant comprises sodium lauroampoacetate, sodium lauroampopropionate, disodium lauroampodiacetate, sodium cocoamphoacetate, disodium cocoamphodiacetate or a mixture thereof.

Suitable Zwitterionic surfactants are known compounds. Any Zwitterionic surfactant that is acceptable for use in the intended end use application and is chemically stable at the required formulation pH is suitable as the optional Zwitterionic surfactant component of the composition of the present invention, including, for example, those which can be broadly described as derivatives of aliphatic quaternary ammonium, phosphonium, and sulfonium compounds in which the aliphatic radicals can be straight chain or branched and wherein one of the aliphatic substituents contains from about 8 to about 24 carbon atoms and one contains an anionic water-solubilizing group such as carboxyl, sulfonate, sulfate, phosphate or phosphonate. Specific examples of suitable Zwitterionic surfactants include alkyl betaines, such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, amidopropyl betaines, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine and alkylamidopropylhydroxy sultaines.

In one embodiment, the personal care composition further comprises an electrolyte, typically in an amount of up to about 20 pbw per 100 pbw of the personal care composition. Suitable electrolytes are known compounds and include salts of multivalent anions, such as potassium pyrophosphate, potassium tripolyphosphate, and sodium or potassium citrate, salts of multivalent cations, including alkaline earth metal salts such as calcium chloride and calcium bromide, as well as zinc halides, barium chloride and calcium nitrate, salts of monovalent cations with monovalent anions, including alkali metal or ammonium halides, such as potassium chloride, sodium chloride, potassium iodide, sodium bromide, and ammonium bromide, alkali metal or ammonium nitrates, and polyelectrolytes, such as uncapped polyacrylates, polymaleates, or polycarboxylates, lignin sulfonates or naphthalene sulfonate formaldehyde copolymers.

In one embodiment, the personal care composition comprises water, an anionic surfactant, a structuring agent for the anionic surfactant, and a pH responsive polymer according to the present invention and exhibits one or more lamellar surfactant phases. "Lamellar surfactant phases" are phases which comprise one or more surfactant bilayers, typically a plurality of surfactant bilayers separated by liquid medium. Lamellar phases include spherulite phases and the typical form of the liquid crystal G-phase, as well as mixtures thereof. "G-phases", which are sometimes referred to in the literature as "$L_\alpha$ phases", are typically pourable, non-Newtonian, anisotropic products that are cloudy looking and exhibit a characteristic "smeary" appearance on flowing. Lamellar phases can exist in several different forms, including domains of parallel sheets, which constitute the bulk of the typical G-phases described above and spherulites formed from a number of concentric spherical shells, each of which is a bilayer of surfactant. In this specification the term "G-phase" will be reserved for compositions, which are at least partly of the former type. The spherulites are typically between 0.1 and 50 microns in diameter and so differ fundamentally from micelles. The surfactant phase morphology of the structured surfactant composition is observed, for example, using an optical microscope under cross-polarized light at about 40× magnification.

In one embodiment, the personal care composition of the present invention exhibits structured surfactant properties, that is, shear-thinning viscosity and a capacity to suspend water insoluble or partially water soluble components As used herein in reference to viscosity, the terminology "shear-thinning" means that such viscosity decreases with an increase in shear rate. Shear-thinning may be characterized as a "non-Newtonian" behavior, in that it differs from that of a classical Newtonian fluid, for example, water, in which viscosity is not dependent on shear rate.

As used herein in reference to a component of an aqueous composition, the terminology "water insoluble or partially water soluble components" means that the component is present in the aqueous composition at a concentration above the solubility limit of the component so that, in the case of a water insoluble component, the component remains substantially non-dissolved in the aqueous composition and, in the case of a partially water soluble component, at least a portion of such component remains undissolved in the aqueous composition.

As used herein, characterization of an aqueous composition as "capable of suspending", or as being "able of suspend" water insoluble or partially water insoluble components means that the composition substantially resists flotation of such components in the composition or sinking of such components in such composition so that such components appear to be neutrally buoyant in such composition and remain at least substantially suspended in such composition under the anticipated processing, storage, and use conditions for such aqueous composition.

In one embodiment, the personal care composition of the present invention comprises, based on 100 pbw of the composition from about 5 to about 40 parts pbw, more typically from about 10 to about 30 pbw, and still more typically from about 15 to about 25 pbw, of the anionic surfactant and from about 0.1 to about 25 pbw, more typically, from about 0.5 to about 10 pbw, of a structuring agent.

In one embodiment, the pH of the lamellar phase containing personal care composition is from about 5.0 to about 7.0, more typically from about 5.5 to about 6.5.

Suitable anionic surfactants include those described above. In one embodiment of the lamellar phase containing personal care composition, the anionic surfactant comprises one or more branched and/or unsaturated anionic surfactants. Suitable branched anionic surfactants, include, for example, sodium trideceth sulfate, sodium tridecyl sulfate, ammonium trideceth sulfate, and ammonium tridecyl sulfate.

Suitable structuring agents include cationic surfactants, amphoteric surfactants, fatty alcohols, alkoxylated alcohols, fatty acids, fatty acid esters, alkanolamides, amine oxides, and electrolytes, and mixtures thereof. An effective amount of such structuring agent is one that promotes and/or does not interfere with the formation of a lamellar surfactant phase. Suitable cationic surfactants, amphoteric surfactants, fatty alcohols, alkoxylated alcohols, fatty acids, fatty acid esters, alkanolamides, amine oxides, and electrolytes are described above.

Typically, the greater the amount of surfactant present in relation to its solubility, the smaller the amount electrolyte that may be required in order to form a structure capable of supporting solid materials and/or to cause flocculation of the structured surfactant. In one embodiment, the composition contains a sufficient amount of an electrolyte to promote formation lamellar surfactant phases.

In one embodiment, the personal care composition of the present invention further comprises, typically in an amount of from greater than 0 pbw to about 50 pbw, more typically form about 1 to about 30 pbw, per 100 pbw of the personal care composition, one or more "benefit agents" that is, materials that provide a personal care benefit, such as moisturizing or conditioning, to the user of the personal care composition, such as, for example, emollients, moisturizers, conditioners, polymers, vitamins, abrasives, UV absorbers, antimicrobial agents, anti-dandruff agents, fragrances, and/or appearance modifying additives, such as, for example, colored particles or reflective particles, which may be in the form of a solid, liquid, or gas and may be insoluble or are only partly soluble in the personal care composition. Mixtures of the benefit agents may be used.

In one embodiment, the personal care composition is a hair styling composition. Suitable hair styling compositions may be in the form of a gel, mousse, or spray and may be applied to the hair and/or skin, for example, by hand or by spraying, as appropriate in view of the form of the composition.

In one embodiment, the personal care composition is a hair styling gel that comprises a hair styling polymer, a pH responsive polymer of the present invention, and a carrier, such as water, a $(C_2-C_6)$alkanol, or a mixture thereof.

Suitable hair styling polymers typically comprise multiple cationic sites per molecule and include, for example, polyquaternium-11, polyquaternium-4, polyquaternium-7, polyquaternium-16, polyquaternium-28, polyquaternium-44, polyquaternium-46, polyquaternium-55, polyquaternium-68 and polyquaternium-88. Suitable hair styling polymers also include, but are not limited to copolymers of polyvinylpyrrolidone, vinyl acetate, polyvinylcaprolactam, methylether maleic acid, acrylamides, octylacrylamide, butylaminoethyl, crotonic acid, dimethylaminopropyl methacrylate and dimethylaminoethyl methacrylate, and mixtures thereof.

As used herein, the term "mousse" means a composition that is in the form of a foam when applied. In one embodiment, the personal care composition is a hair styling mousse is packaged in a pressurized container and comprises a hair styling polymer, a pH responsive polymer of the present invention, a carrier, such as water, a $(C_2-C_6)$alkanol, a propellant suitable for foaming the composition when the composition is dispensed from the container. Suitable propellants are liquefiable gases, such as, for example, propane, butane, isobutane, nitrogen, carbon dioxide, nitrous oxide, 1,2-difluoroethane.

In one embodiment, the personal care composition is a hair spray composition suitable for spray application from a container that is equipped with a mechanical sprayer, comprising a hair styling polymer, a pH responsive polymer of the present invention, and a carrier, such as water, a $(C_2-C_6)$alkanol, or a mixture thereof.

In one embodiment, the personal care composition is an aerosol hair spray composition suitable for spray application from a pressurized container and comprises, a hair styling polymer, a carrier, typically a $(C_1-C_6)$alkanol or a $(C_7-C_{10})$ isoparaffin, a pH responsive polymer of the present invention, and a propellant suitable for aerosol delivery of the hair spray composition to the hair. Suitable propellants are those described above in regard to the hair styling mousse embodiment of the personal care composition of the present invention.

The hair styling gel, mousse, and hair spray may in each case, optionally further comprise one or more emollients, conditioning agents, shine enhancers, moisture and heat sensitive moieties, or a mixture thereof. Suitable emollients include, for example, PEG-40 castor oil, glycerol, propylene glycol, butylene glycol. Suitable conditioning and shine agents include, for example, quaternized and/or hydrolyzed proteins of honey, soy, wheat, guar or maize, cetyl alcohol, stearyl alcohol, ceteareth-20, isopropyl palmitate, cyclopentasiloxane, cyclomethicone, trimethylsilyamodimethicone, phenyltrimethicone, ethoxylated/propylated dimethicone, dimethiconol, panthenol, tocopherol acetate, tocopherol, cetrimmonium chloride, hair keratin and silk amino acids and ethoxylated/propoxylated waxes of fruit and vegetable origin.

The personal care composition according to the present invention may optionally further comprise one or more adjuvants, such as, for example, preservatives such as benzyl alcohol, methyl paraben, propyl paraben and imidazolidinyl urea; pH adjusting agents such as citric acid, succinic acid, phosphoric acid, sodium hydroxide, sodium carbonate; dyes, and sequestering agents such as disodium ethylenediamine tetra-acetate.

In general, personal care compositions may optionally comprise, based on 100 pbw of the personal care composition and independently for each such adjuvant, from about 0 to about 10 pbw, typically from 0.5 pbw to about 5.0 pbw, of such optional adjuvants, depending on the desired properties of the personal care composition.

The pH responsive polymer of the present application is useful as a component in aqueous fluid compositions used in oilfield applications.

In one embodiment, an aqueous fluid composition of the present invention comprises water and a pH responsive polymer of the present invention, typically from about 0.05 to about 40 pbw, more typically 0.1 pbw to 20 pbw, even more typically form about 1 to about 10 pbw of the pH responsive polymer per 100 pbw composition, wherein the pH of the composition is greater than or equal to about 6, more typically, from about 6 to about 10.

In one embodiment, the aqueous fluid composition further comprises one or more salts. The salt may be intentionally added as a component of the composition or may be present in a geologic formation and become dissolved in the composition when the composition is contacted with the formation.

In one embodiment, the aqueous fluid composition of the present invention is used in a method for handling of particles of debris, typically mineral particles, generated during the excavation, such as during digging, boring, drilling, blasting, dredging, or tunneling, of a geologic formation in the course of constructing a structure, such as for example, a road, bridge, building, mine, or tunnel, or drilling an oil and/or gas well. The particles generally have a particle size ranging from a fine powder to coarse gravel, e.g. dust, sand, and gravel. The debris particles are mixed with the aqueous fluid composition to form an aqueous particle dispersion and the aqueous particle dispersion is transported as needed by, for example, pumping the dispersion through a conduit. Such particle dispersions typically contain, based on 100 pbw of the liquid component of the dispersion, 90 pbw to about 99.9 pbw water, from about 0.1 pbw to about 10 pbw pH responsive polymer, and from about 5 pbw to about 150 pbw mineral particles. The particle handling method is useful in known particle handling applications, such as, for example, to transport and place mineral processing waste in underground caverns, to backfill open pits or quarries, to place clay or other liners in holding or storage, to extinguish and/or contain coal mine fires by deploying quantities of solids below ground to seal the fire from sources of oxygen, and to fill previously mined cavities with solids to prevent surface subsidence.

In one embodiment, the aqueous fluid composition of the present invention is used as the fracturing fluid in a method for hydraulic fracturing of a geologic formation to stimulate the production of fluids, such as oil and/or natural gas, from the formation. The fracturing fluid is injected through a wellbore and against a surface of the formation at a pressure and flow rate at least sufficient to initiate and/or extend one or more fractures in the formation. Typically, the fracturing fluid further comprises a proppant dispersed in the fracturing fluid. Suitable proppants are inorganic particles, such as sand, bauxite particles, or glass beads and are typically in the range of from about 20 to about 40 mesh. Such fracturing fluid compositions typically contain, based on 100 pbw of the liquid component of such composition, from about 90 pbw to about 100 pbw water, from about 0.1 pbw to about 10 pbw pH responsive polymer, and from about 10 pbw to about 150 pbw proppant. The proppant particles are transported into fractures in the geologic formation by the pressurized fracturing fluid stream and keep the fractures from closing back down when the stream of fracturing fluid is discontinued. The proppant-filled fractures provide permeable channels through which the formation fluids can flow to the wellbore and then be withdrawn. Hydraulic fracturing fluids are subject to high temperatures and shear rates.

Another novel aspect of the present invention are the compounds, i.e., monomers, corresponding to structures III and V. While the HASE polymers according to the present invention as described above have the compounds, the compounds may also be polymerized or copolymerized with other monomers, including those disclosed above, to form yet different polymers and copolymers. The different polymers and copolymers can be obtained by polymerization or copolymerization in the manner described above for the HASE polymers.

This (co)polymerization may also be conducted by different methods or in different solvents. The scope of methods and solvents is well known to those skilled in the art.

An example of the prevent invention is set forth below. Unless otherwise indicated, all parts, percentages, and proportions herein are by weight.

Example 1

Monomer Synthesis

The monomer of Example 1A, according to structure (XXI), which is referred to as "ODD":

is made as follows. 2-Octyl-1-dodecanol ethoxylate (25 moles of ethylene oxide per mole, 214 g=0.15 mol) is charged to a 500 ml round-bottom 5-neck glass flask equipped with a PTFE blade agitator, temperature sensor, dry compressed air purge line and a water cooled condenser. The liquid ethoxylate is warmed to 69° C., stirred, and MEHQ (0.35 g=0.0027 mol) is then added. A purge of dry air at approximately 20 ml min$^{-1}$ is passed through the liquid and five minutes later methacrylic anhydride (46.7 g=0.303 mol) is added. The temperature is stabilized and held between 70-73° C. for five hours, then the liquid is cooled to 40° C. Methacrylic acid (35.0 g=0.407 mol) and water (67.0 g=3.72 mol) are added and the liquid product is discharged.

The monomer of Example 1B according to structure (XXII), which is referred to as "NOPOL":

is made as follows Nopol alkoxylate (Nopol compound according to structure (XVI) above, alkoxylated with 5 moles propylene oxide and 25 moles ethylene oxide per mole, 201.5 g=0.129 mol) is charged to a 500 ml round-bottom 5-neck glass flask equipped with a PTFE blade agitator, temperature sensor, dry compressed air purge line and a water cooled condenser. The liquid ethoxylate is warmed to 66° C., stirred, and MEHQ (0.37 g=0.0030 mol) is added. A purge of dry air at approximately 20 ml min$^{-1}$ is passed through the liquid and twelve minutes later methacrylic anhydride (40.3 g=0.262 mol) is added. The temperature is stabilized and held between 70-74° C. for five and a half hours, then the liquid is cooled to 41° C. Methacrylic acid (38.0 g=0.442 mol) and water (65.0 g=3.61 mol) are added and the liquid product is discharged.

Example 2

Preparation of HASE Systems

The HASE polymers of Examples 2A and 2B and the HASE polymer of Comparative Example C2 are each made according to the procedure set forth below.

Add heat to kettle charge to about 80° C. while purging with N$_2$. Maintain N$_2$ blanket throughout run. At about 80° C., add 25% Initiator solution and 2% Monomer emulsion. Hold at that temperature for about 15 minutes. Feed remainder of monomer emulsion and initiator solution over 3 hours. Hold for 30 minutes, and add the chaser solution. Finally, heat to about 80° C. and hold for 30 minutes, and allow to cool. The ingredients used are shown in TABLE I below.

TABLE I

| Materials | Ingredient weight (g) | % BOTM* |
|---|---|---|
| Kettle Charge | | |
| Deionized Water | 120.00 | |
| Rhodapex AB20 @ 29.0% | 0.41 | 0.12 |
| Ammonium persulfate | 0.18 | 0.18 |
| Monomer Emulsion | | |
| Deionized Water | 67.83 | |
| Rhodapex AB20 @ 29.0% | 6.90 | 2 |
| Methyl acrylic acid (MAA) | 40.00 | 40 |
| Ethyl acrylate (EA) | 56.00 | 56 |
| Component C 60.1% | 6.66 | 4 |
| Initiator Solution | | |
| Deionized Water | 40.00 | |
| Ammonium Persulfate | 0.25 | 0.25 |
| Chaser Solution | | |
| Ammonium persulfate | 0.18 | 0.18 |
| Deionized water | 3.00 | |
| Total | 341.41 | |

*% BOTM means percentage based on total monomer weight.

The following hydrophobic monomers (Component C) are employed:

Component C of the reaction mixture used to make the polymer of Example 2A was an ODD monomer according to structure (XXI), Component C of the reaction mixture used to make the polymer of Example 2B was a NOPOL monomer according to structure (XXII), and Component C of the reaction mixture used to make the polymer of Comparative Example C2 was SIPOMER™ BEM monomer (behenyl methacrylate, Rhodia Inc.)

Example 3

Latex Coatings

The HASE polymers of Examples 3A, 3B and C3-1 (each analogous to a respective one of the polymers described in Examples 2A, 2B, and C2 above), were each then mixed with a paint latex (VALSPAR 153-16 by Valspar Corp.) in the necessary quantities to reach a Stormer viscosity of 95 KU (Krebbs Units). The mixtures were tested for viscosity versus shear rate The viscosity (in units of Pascal seconds ("Pa s") at very low shear rate (film formation) are given in TABLE II below.

TABLE II

| EX # | Analogous to polymer of Example: | Component C of HASE polymer | Viscosity (Pa s) |
|---|---|---|---|
| C3-1 | C2 | SIPOMER BEM* | 469 |
| 3B | 2B | NOPOL (monomer according to structure (XXII)) | 173 |
| 3A | 2A | ODD (monomer according to structure (XXI)) | 96 |

*formed polymer and paint latex mixture not of the present invention.

Figure 1:
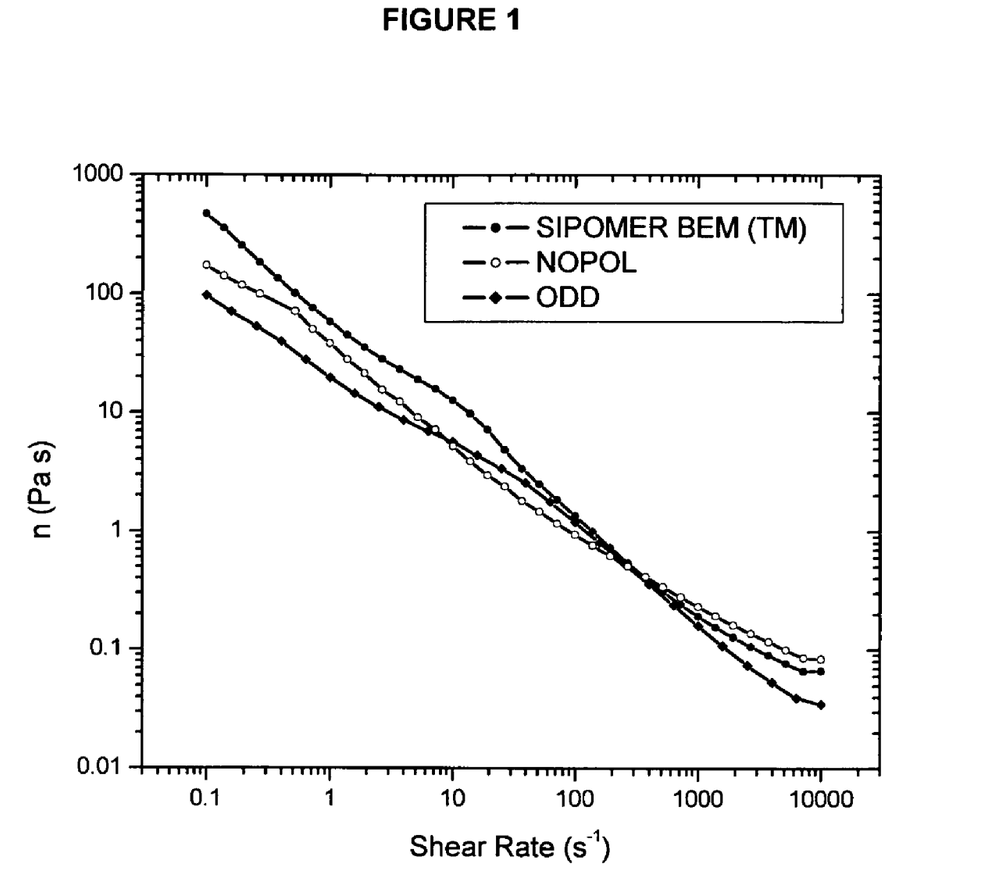
FIG. 1 is a plot diagram of the viscosity profiles of HASE polymer/paint latex mixtures of the present invention.

The mixtures of the invention exhibited useful viscosity profiles in the low (0.1 to 7 s−1), medium (7-1000 s−1) and high (1000-10000 s−1) shear rates compared to the comparative mixture. These shear rate ranges correspond to those commonly encountered during film formation, formulation appearance/mixing and application (spraying, brushing). Viscosity profiles are shown in FIG. 1.

Figure 2:
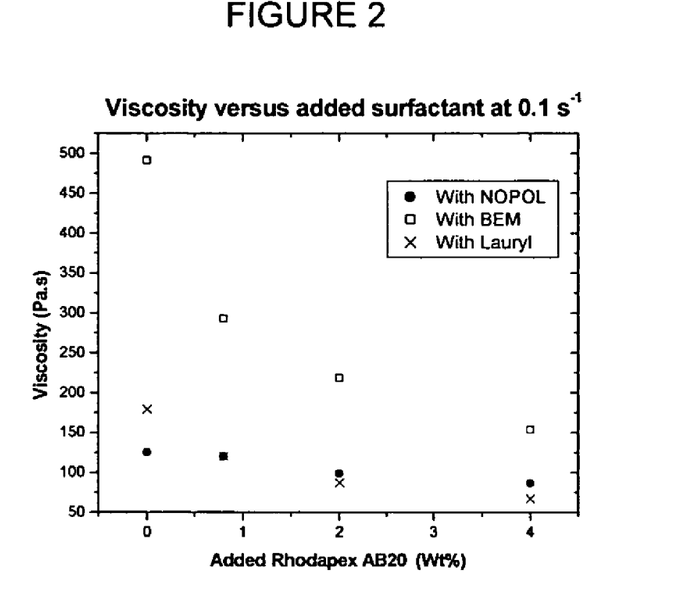
FIG. 2 shows the viscosity at $0.1\ s^{-1}$ shear rate as a function of added surfactant for HASE polymer/paint latex mixtures of the present invention.
Figure 3:
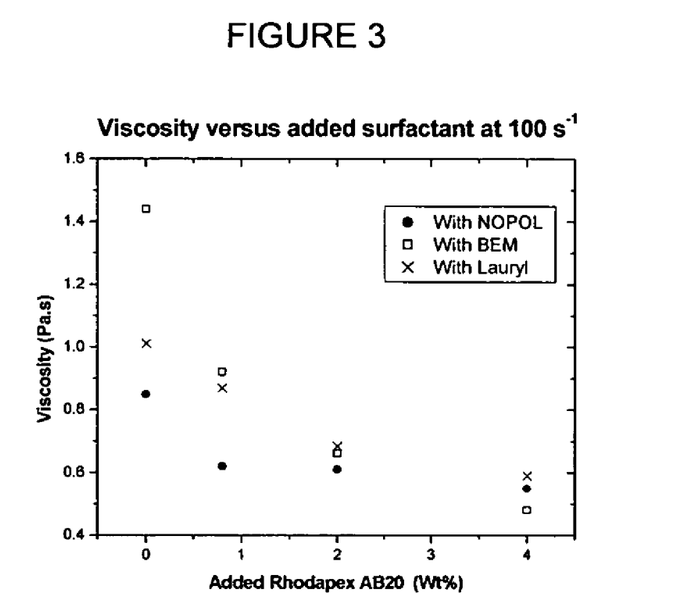
FIG. 3 shows the viscosity at $100\ s^{-1}$ shear rate as a function of added surfactant for HASE polymer/paint latex mixtures of the present invention.
Figure 4:
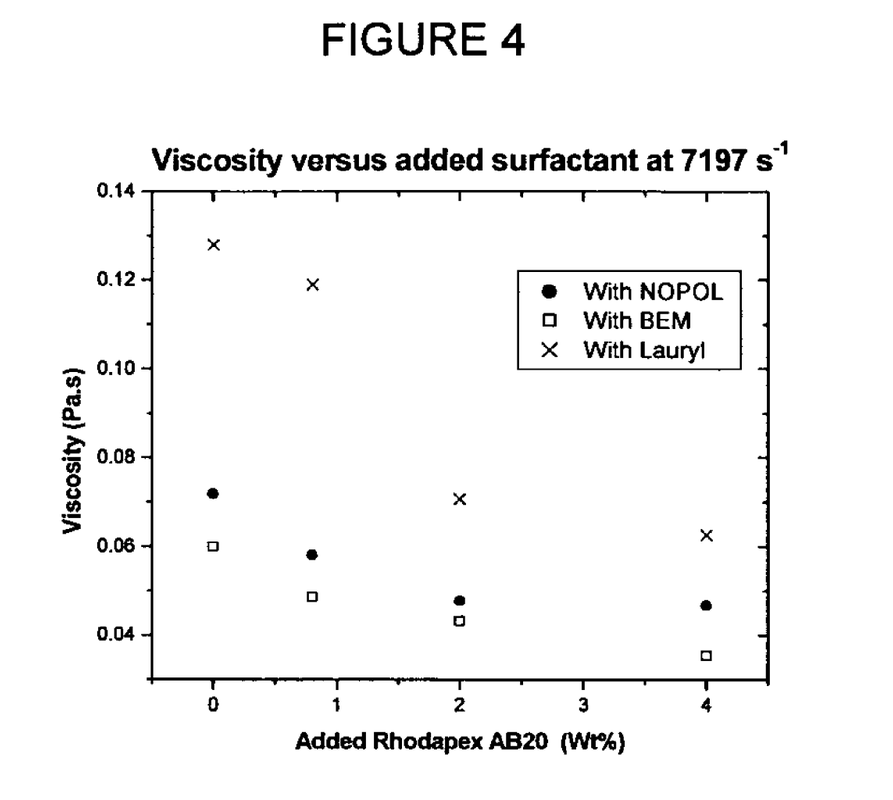
FIG. 4 shows the viscosity at $7197\ s^{-1}$ shear rate as a function of added surfactant for HASE polymer/paint latex mixtures of the present invention.

Nopol based HASE polymers present an excellent consistency of viscosity toward the addition of surfactants. This property is of particular interest when surface active ingredients are post-added to a thickened base paint system. FIGS. 2, 3, and 4 show the viscosity at different shear rates (0.1; 100; and 7197 s$^{-1}$) as a function of added surfactant (Rhodapex AB20) for an acrylic latex (Valspar15316) thickened with Nopol, BEM (C22 hydrophobe) and Lauryl (C12 hydrophobe) based HASE polymers (Stormer viscosity between 95-110 Krebbs Units ("KU").

The Nopol thickened system presents an excellent consistency of viscosity toward added surfactant at low shear rate (sagging range). Its viscosity remains quasi-constant while the viscosity of BEM drops from ca. 500 Pas. to ca. 150 Pas. with 4 Wt. % added surfactant. This good viscosity consistency is still visible at 100 s$^{-1}$ (texture, appearance range) while in the high shear rate range (7197 s$^{-1}$ data, processing range) the lauryl based HASE thickened systems presents the higher sensitivity.

The composition of Example 3C was made by thickening a paint latex (30% solids) to a Stormer viscosity of 95 KU using a HASE polymer analogous to that described in Example 2B above. The composition of Comparative Example C3-2 was made by thickening an analogous paint latex (30% solids) a Stormer viscosity of 95 KU using a commercially available HASE polymer. Surfactant (sodium dodecyl sulfate (SDS)) was added to the compositions of Examples 3C and C3-2 and the Stormer viscosity (in Krebbs Units) was measured. Results are given in TABLE III A and B below.

TABLE III A

Viscosity for Example 3C

| SDS (wt %) | Stormer Viscosity (KU) |
|---|---|
| 0.00 | 94.4 |
| 0.17 | 92.2 |
| 0.35 | 89.3 |
| 0.53 | 87.6 |
| 0.70 | 85.9 |
| 1.97 | 79.9 |

TABLE III B

Viscosity for Comparative Example C3-2

| SDS (wt %) | Stormer Viscosity (KU) |
|---|---|
| 0.00 | 95.3 |
| 0.18 | 76.6 |
| 0.34 | 68.1 |
| 0.52 | 63.3 |
| 0.69 | 60.6 |
| 1.97 | 53.06 |

The viscosity of the composition of Example 3C was less sensitive to addition of the surfactant than was that of Comparative Example C3-2.

Examples 4 to 14 and Comparative Examples C4 to C14

Personal Care Compositions

Each of Examples 4 to 14 include a polymer according to the present invention (analogous to that of Example 2B above) derived from a mixture of 40 wt % methacrylic acid, 56 wt % ethyl acrylate, and 4 wt % of a NOPOL monomer according to structure (XXII) and having a number average molecular weight of about 400,000 daltons).

The personal care compositions of Comparative Examples C4 to C7 were made by mixing together the relative amounts (as wt %) of the materials set forth in TABLE III below. The personal care compositions of Examples 4 to 7 were made by adding the polymer according to the present invention to a respective one of the compositions of Comparative Examples C4 to C7.

The personal care compositions of Examples 4 to 7 and Comparative Examples C4 to C7 were evaluated by visual inspection to determine if the composition contained suspended air bubbles. The results of the evaluation are given in TABLE IV below.

TABLE IV

|  | Ex C4 | EX C5 | Ex C6 | Ex C7 |
|---|---|---|---|---|
| Ammonium laureth sulfate | 14.5 | 14.5 | 14.5 | 14.5 |
| cocomonoethanolamine | 2.1 | 2.1 | 2.1 | 2.1 |
| Ammonium xylene sulfonate | 0.8 | 0.8 | 0.8 | 0.8 |
| Hydroxypropyl guar (Jaguar HP-60, Rhodia inc.) | — | 0.3 | — | — |
| Xanthan gum (Rhodicare T, Rhodia Inc.) | — | — | 0.3 | — |
| Acrylates/($C_{10}$-$C_{30}$)alkyl acrylate cross-polymer (Carbopol ETD-2020) | — | — | — | 0.3 |
| Water | 82.2 | 81.9 | 81.9 | 81.9 |
| Preservative (Glydant) | 0.4 | 0.4 | 0.4 | 0.4 |
| Suspends air bubbles? | No | No | Partially | No |

|  | Ex 4 | Ex 5 | Ex 6 | Ex 7 |
|---|---|---|---|---|
| Ex C1 | 90.1 | | | |
| EX C2 | | 90.1 | | |
| EX c3 | | | 90.1 | |
| Ex C4 | | | | 90.1 |
| polymer according to present invention | 9.9 | 9.9 | 9.9 | 9.9 |
| Suspends air bubbles? | Yes | Yes | Yes | Yes |

The personal care compositions of Comparative Examples C8 and C9 were made by mixing together the relative amounts (as wt %) of the materials set forth in TABLE IV below. The personal care compositions of Examples 8 and 9 were made by adding the polymer according to the present invention to a respective one of the compositions of Comparative Examples C8 and C9.

The personal care compositions of Examples 8 and 9 and Comparative Examples C8 and C9 were evaluated by visual inspection to determine if the composition separated into layers. The results of the evaluation are given below in TABLE V below.

TABLE V

|  | Ex C8 | Ex C9 |
|---|---|---|
| Ammonium laureth sulfate | 13.2 | 13.2 |
| Cocomonoethanolamine | 1.9 | 1.9 |
| Ammonium xylene sulfonate | 0.7 | 0.7 |
| Hydroxypropyl Guar (Jaguar HP-60, Rhodia inc.) | 0.3 | |
| Acrylates/($C_{10}$-$C_{30}$)alkyl acrylate cross-polymer (Carbopol ETD-2020 | | 0.3 |
| Water | 74.4 | 74.4 |
| Preservative (Glydant) | 0.4 | 0.4 |
| Sunflower Oil | 9.1 | 9.1 |
| Stability | separated | separated |

|  | Ex 8 | Ex 9 |
|---|---|---|
| EX C5 | 91 | |
| EX C6 | | 91 |
| polymer according to present invention | 9 | 9 |
| Stability | no separation | no separation |

A clear conditioning bodywash with suspended oil droplets (Example 10) was made by mixing together the following materials in the relative amounts (as percent by weight ("wt %")) given below:

| Ingredient | Amount (wt %) |
|---|---|
| polymer according to present invention | 2 |
| Ammonium laureth sulfate | 8.4 |
| Ammonium xylene sulfonate | 0.5 |
| Cocomonoethanolamine | 2 |
| Mineral oil | 1 |
| Hydroxypropyl guar hydroxypropyltrimonium chloride | 0.2 |
| Triethanolamine, fragrance, preservative | q.s. |
| Water | q.s. |

The composition of Example 10 exhibited a viscosity of 920 cP. Visible oil droplets in the composition of Example 10 remained stable and suspended after 1 month at 45° C. An analogous composition (Comparative Example C10) which lacked the polymer according to the present invention, but which included 1 wt % hydroxypropyl guar exhibited a viscosity of 4200 cP, but showed oil separation after 1 month at 45° C.

A clear conditioning bodywash with suspended exfoliating beads (Example 11) was made by mixing together the following materials in the relative amounts (as wt %) given below:

| Ingredient | Amount (wt %) |
|---|---|
| polymer according to present invention | 2 |
| Ammonium laureth sulfate | 8.4 |
| Ammonium xylene sulfonate | 0.5 |
| Cocomonoethanolamine | 1.2 |
| Disodium Laureth Sulfosuccinate | 2.5 |
| Induchem Unispheres | 1 |
| Hydroxypropyl Guar Hydroxypropyltrimonium chloride | 0.2 |
| Triethanolamine, fragrance, preservative | q.s. |
| Water | q.s. |

The composition of Example 11 exhibited a viscosity of 790 cP. Large dense beads remained stable and suspended in the composition of Example 11 after 1 month at 45° C. An analogous composition (Comparative Example C11) which lacked the polymer according to the present invention, but included 1 wt % hydroxypropyl guar exhibited a viscosity of 3940 cP. Beads sedimented from the composition of Comparative Example C11 after 1 month at 45° C.

A clear shampoo with suspended oil droplets (Example 12) was made by mixing together the following materials in the relative amounts (as wt %) given below:

| Ingredient | Amount (wt %) |
| --- | --- |
| polymer according to present invention | 2 |
| sodium laureth sulfate | 4.2 |
| Cocomonoethanolamine | 0.8 |
| Hydroxypropyl Guar | 0.2 |
| Hydroxypropyltrimonium chloride | |
| Safflower oil | 1.0 |
| Triethanolamine, fragrance, preservative | q.s. |
| Water | q.s. |

The composition of Example 12 exhibited a viscosity of 860 cP, Visible oil droplets remained stable and suspended in the composition of Example 12 after 1 month at 45 C. An analogous composition (Comparative Example C12) which lacked the polymer according to the present invention, but included 1 wt % hydroxypropyl guar exhibited a viscosity of 5820 cP. Oil separated from the composition of Comparative Example C12 after 1 month at 45° C.

A clear conditioning hair-spray gel with suspended oil droplets (Example 13) was made by mixing together the following materials in the relative amounts (as wt %) given below:

| Ingredient | Amount (wt %) |
| --- | --- |
| polymer according to present invention | 2 |
| Sodium laureth sulfate | 0.6 |
| Hydroxypropyl Guar | 0.1 |
| Hydroxypropyltrimonium chloride | |
| Amodimethicone | 0.2 |
| Sodium Laureth-13 Carboxylate | 0.2 |
| Mineral Oil | 1 |
| Polyvinylpyrolidone | 5 |
| Triethanolamine, fragrance, preservative | q.s. |
| Water | q.s. |

The composition of Example 13 exhibited a viscosity of 830 cPs Visible oil droplets remained stable and suspended in the composition of Example 13 after 1 month at 45° C. An analogous composition (Comparative Example C13) which lacked the polymer according to the present invention, but included 1 wt % hydroxypropyl guar exhibited a viscosity of 3950 cP. Oil separated from the composition of Comparative Example C13 after 1 month at 45° C.

A clear conditioning hair gel with suspended oil droplets (Example 14) was made by mixing together the following materials in the relative amounts (as wt %) set forth below:

| Ingredient | Amount (wt %) |
| --- | --- |
| polymer according to present invention | 2 |
| sodium laureth sulfate | 0.3 |
| Hydroxypropyl Guar | 0.1 |
| Hydroxypropyltrimonium chloride | |
| PEG/PPG 10/2 dimethicone | 0.4 |
| Safflower oil | 1 |
| Polyvinylpyrolidone | 5 |
| Triethanolamine, fragrance, preservative | q.s. |
| Water | q.s. |

The composition of Example 14 exhibited a viscosity of 790 cP. Visible oil droplets remained stable and suspended in the composition of Example 14 after 1 month at 45 C. An analogous composition (Comparative Example C14) which lacked the polymer according to the present invention but included 1 wt % hydroxypropyl guar exhibited a viscosity of 3290 cP. Oil separated from the composition of Comparative Example C14 after 1 month at 45° C.

Example 15

Oilfield

The composition of Example 15 was made to evaluate possible use of a polymer according to the present invention derived from a mixture of 40 wt % methacrylic acid, 56 wt % ethyl acrylate, and 4 wt % of a NOPOL monomer according to structure (XXII) and having a number average molecular weight of about 400,000 daltons, as a component in an aqueous composition for high temperature, high shear rate oilfield applications.

Deionized water was mixed with sodium bicarbonate to make a 300 ppm sodium bicarbonate hardness water. 88 ml of the DI water/sodium bicarbonate mixture was placed in a laboratory blender and 12 ml of a latex of the polymer according to the present invention (analogous to the polymer latex of Example 2B above and containing about 30% solids) was added to the mixture while mixing to make an aqueous polymer composition that exhibited a low viscosity and a milky white appearance.

The pH of the composition was then adjusted to about 6.8 by addition of about 0.6 ml of 50% sodium hydroxide. Upon adjustment of the pH, the composition became more viscous and changed in appearance from milky white to clear and colorless. The composition was then centrifuged to remove any bubbles.

A sample of about 30 ml of the aqueous polymer composition was placed in the sample cup of a Brookfield PVS high pressure, high temperature viscometer and the viscosity of the sample was measured as a function of shear rate at several temperatures from 75° F. to 325° F., in 25° F. increments. The pressure was maintained at 400 pounds per square inch ("psi"). The sample exhibited good shear thinning behavior up to 300° F. The results are tabulated in the TABLE VI below, as viscosity ("$\eta$"), in centiPoise ("cP"), and Shear Rate ("$\sigma$"), in reciprocal seconds ("$sec^{-1}$"), at several different temperatures ("T"), in degrees Fahrenheit ("F").

TABLE VI

Viscosity, $\eta$, for Composition of Example 15 at Shear Rate, $\sigma$, and Different Temperatures

| | $\eta$ (cP) @ T | | | | | |
| --- | --- | --- | --- | --- | --- | --- |
| $\sigma$ ($sec^{-1}$) | 75° F. | 100° F. | 125° F. | 150° F. | 175° F. | 200° F. |
| 0.04 | 172256 | 157243 | 180158 | 150132 | 135909 | 108253 |
| 0.07 | 139788 | 119172 | 141296 | 101070 | 90510 | 63147 |
| 0.10 | 101188 | 80365 | 84594 | 67675 | 61494 | 48743 |
| 0.21 | 50757 | 42297 | 44575 | 37254 | 32729 | 25541 |
| 0.40 | 29751 | 24555 | 24136 | 19946 | 18353 | 14582 |
| 0.70 | 17315 | 15151 | 14766 | 12169 | 11351 | 9057 |
| 1.01 | 12995 | 11196 | 10425 | 9030 | 8030 | 6631 |
| 2.00 | 7498 | 6338 | 5902 | 5111 | 4522 | 3816 |
| 4.00 | 4524 | 3746 | 3391 | 2917 | 2590 | 2216 |
| 7.01 | 2948 | 2459 | 2172 | 1895 | 1663 | 1429 |
| 10.00 | 2260 | 1887 | 1666 | 1432 | 1257 | 1099 |
| 20.00 | 1434 | 1177 | 1021 | 885 | 774 | 665 |
| 40.00 | 929 | 776 | 649 | 559 | 481 | 419 |

TABLE VI-continued

Viscosity, η, for Composition of Example 15 at Shear Rate, σ, and Different Temperatures

| 69.99 | 695 | 564 | 470 | 400 | 343 | 295 |
| 99.95 | 497 | 468 | 386 | 328 | 282 | 241 |
| 199.99 | 429 | 338 | 273 | 229 | 193 | 165 |
| 399.99 | 323 | 253 | 201 | 166 | 140 | 118 |

| | η (cP) @ T | | | | |
|---|---|---|---|---|---|
| σ (sec$^{-1}$) | 225° F. | 250° F. | 275° F. | 300° F. | 325° F. |
| 0.04 | 82177 | 51361 | 30817 | 1580 | |
| 0.07 | 44531 | 32181 | 18102 | 5531 | |
| 0.10 | 35139 | 23751 | 11388 | 1728 | |
| 0.21 | 20325 | 11713 | 6546 | 2499 | |
| 0.40 | 10979 | 8680 | 4751 | 1697 | |
| 0.70 | 6782 | 4954 | 2886 | 1683 | 337 |
| 1.01 | 4831 | 3822 | 1877 | 1038 | 436 |
| 2.00 | 2858 | 2186 | 1244 | 403 | 235 |
| 4.00 | 1771 | 1301 | 737 | 427 | 293 |
| 7.01 | 1117 | 863 | 585 | 278 | 120 |
| 10.00 | 873 | 702 | 450 | 212 | 111 |
| 20.00 | 546 | 432 | 297 | 161 | 60 |
| 40.00 | 343 | 273 | 196 | 111 | 62 |
| 69.99 | 242 | 197 | 145 | 83 | 44 |
| 99.95 | 196 | 161 | 123 | 70 | 40 |
| 199.99 | 137 | 112 | 88 | 55 | 32 |
| 399.99 | 97 | 81 | 65 | 42 | 27 |

The present invention has been described with particular reference to the preferred embodiments. It will be obvious to one of ordinary skill in the art that changes and modifications may be made to the above description without departing from the spirit and scope of the invention.

What is claimed is:

1. An emulsion, comprising:
   a) a latex polymer,
   b) a pH responsive polymer comprising, based on the total weight of monomers,
      (i) from about 25 to about 70 percent by weight acid monomeric units, each independently comprising a carboxylic acid-functional substituent group,
      (i) from about 30 to about 70 percent by weight nonionic monomeric units, each independently comprising a nonionic substituent group, and
      (iii) from about 0.05 to about 20 percent by weight hydrophobic monomeric units, each independently derived from a monomer according to structure (XXI) or structure (XXII):

(XXI)

(XXII)

and
   c) an emulsifier, and
   d) water.

2. The emulsion of claim 1, wherein the emulsion is selected from the group consisting of a latex paint, a latex coating, a cosmetic, a detergent/cleanser, and an oilfield drilling fluid.

3. The emulsion of claim 1, wherein the emulsion is a latex paint.

4. The emulsion of claim 1, wherein the hydrophobic monomeric units of the pH responsive polymer comprise monomeric units derived from a monomer according to structure (XXI).

5. The emulsion of claim 1, wherein the hydrophobic monomeric units of the pH responsive polymer comprise monomeric units derived from a monomer according to structure (XXII).

6. The emulsion of claim 1, wherein the pH responsive polymer is present in an amount effective for modifying the rheological properties of the emulsion.

7. The emulsion of claim 3, wherein the emulsion is a latex paint comprising, based on the total weight of the latex paint, from about 0.05 to about 5.0 weight percent the pH responsive polymer.

* * * * *